United States Patent
Baseeth et al.

(10) Patent No.: US 9,416,065 B2
(45) Date of Patent: Aug. 16, 2016

(54) ADJUVANTS AND METHODS OF USING THEM

(75) Inventors: Shireen Baseeth, Decatur, IL (US); Bruce Sebree, Oakley, IL (US)

(73) Assignee: Archer Daniels Midland Company, Decatur, IL (US)

( * ) Notice: Subject to any disclaimer, the term of this patent is extended or adjusted under 35 U.S.C. 154(b) by 464 days.

(21) Appl. No.: 12/025,833

(22) Filed: Feb. 5, 2008

(65) Prior Publication Data

US 2008/0194410 A1    Aug. 14, 2008

Related U.S. Application Data

(60) Provisional application No. 60/889,422, filed on Feb. 12, 2007.

(51) Int. Cl.
| | |
|---|---|
| *C05G 3/00* | (2006.01) |
| *C05G 3/06* | (2006.01) |
| *A01N 25/30* | (2006.01) |
| *A01N 25/02* | (2006.01) |
| *A01N 25/04* | (2006.01) |
| *A01N 25/06* | (2006.01) |
| *A01N 57/20* | (2006.01) |

(52) U.S. Cl.
CPC ............... *C05G 3/007* (2013.01); *A01N 25/30* (2013.01); *C05G 3/06* (2013.01)

(58) Field of Classification Search
CPC ........... C05G 3/007; C05G 3/06; A01N 25/30
See application file for complete search history.

(56) References Cited

U.S. PATENT DOCUMENTS

| | | | | |
|---|---|---|---|---|
| 4,711,902 | A | * | 12/1987 | Serno ............................ 514/356 |
| 5,260,260 | A | | 11/1993 | Gednalske et al. |
| 5,482,529 | A | | 1/1996 | Ahlnas et al. |
| 5,514,670 | A | * | 5/1996 | Friedman et al. .......... 424/185.1 |
| 5,547,988 | A | * | 8/1996 | Yu et al. ........................ 514/557 |
| 6,309,663 | B1 | * | 10/2001 | Patel et al. .................... 424/450 |
| 6,348,434 | B1 | | 2/2002 | Schmidt |
| 6,716,473 | B2 | * | 4/2004 | Bodnar et al. ................ 426/602 |
| 6,797,673 | B1 | | 9/2004 | Worthley et al. |
| 8,282,950 | B2 | | 10/2012 | Bohus et al. |
| 2002/0160916 | A1 | | 10/2002 | Volgas et al. |
| 2004/0077703 | A1 | * | 4/2004 | Soll et al. ...................... 514/410 |
| 2005/0170967 | A1 | * | 8/2005 | Parrish et al. ................. 504/362 |
| 2005/0232953 | A1 | * | 10/2005 | Barnikol ............... A61K 8/064 424/400 |

(Continued)

FOREIGN PATENT DOCUMENTS

| | | |
|---|---|---|
| EP | 0099039 A1 | 1/1984 |
| EP | 0577914 A1 | 1/1994 |

(Continued)

OTHER PUBLICATIONS

Lecithin [online] retrieved from http://www.merriam-webster.com/dictionary/lecithin on Oct. 29, 2010.*

(Continued)

*Primary Examiner* — Ernst V Arnold
*Assistant Examiner* — Kyung Sook Chang
(74) *Attorney, Agent, or Firm* — Andrew Nilles; Alexandra Lakshwanan

(57) ABSTRACT

Described herein are compositions comprising an acidifier intermixed with an emulsifier and a co-surfactant that form stable microemulsions in water. Also described are methods of dispersing a compound in an aqueous solution using the compositions of the present invention.

5 Claims, 5 Drawing Sheets

(56) References Cited

U.S. PATENT DOCUMENTS

| | | | |
|---|---|---|---|
| 2006/0180677 A1 | | 8/2006 | McManic et al. |
| 2007/0078057 A1* | | 4/2007 | Rowley et al. .............. 504/206 |
| 2007/0131010 A1 | | 6/2007 | Binder et al. |

FOREIGN PATENT DOCUMENTS

| | | | | |
|---|---|---|---|---|
| WO | 8908628 A1 | | 9/1989 | |
| WO | WO98/48624 A1 | | 11/1998 | |
| WO | 0126463 A1 | | 4/2001 | |
| WO | WO 03/059063 A1 * | | 7/2003 | ............ A01N 37/00 |
| WO | 2007008557 A1 | | 1/2007 | |
| WO | 2007030649 A2 | | 3/2007 | |
| WO | 2008085232 A2 | | 7/2008 | |

OTHER PUBLICATIONS

Vertellus Castor Oil and its Chemistry ([online]; retrieved from: http://www.groshea.com/pdf/white%20papers/beanbookchemistry.pdf; on Jun. 27, 2011; 2 pages).*

Scientific Psychic "Fats, Oils, Fatty Acids, Triglycerides—Chemical Structure" (scientificpsychic.com/fitness/fattyacids1.html, last visit Aug. 16, 2013).*

Emulsifiers with HLB values, [retrieved from www.theherbarie.com/files/resource.../Emulsifiers_HLB_Values.pdf, last visit Apr. 30, 2015].*

American Lecithin Company (ALC), "Lecithins and Phospholipids", pp. 1-19, 2009 [retrieved from on-line website (http://www.americanlecithin.com/lecithin_2009, last vist, Aug. 17, 2015)].*

Spernath et al. "Fully dilutable microemulsions embedded with phospholipids and stabilized by short-chain organic acids and polyols", Journal of Colloid and Interface Science 299 (2006) pp. 900-909.*

Schofield et al., "Compositions of Soybean Lecithin", Journal of the American Oil Chemists' Society, vol. 58, No. 10 (Oct. 1981), pp. 889-892.*

Szubaj, "Lecithins: Sources, Manufacture & Uses", American Oil Chemists' Society (1989), pp. 156, 166 and 167.*

Written Opinion of the International Searching Authority and International Search Report for International Application No. PCT/US2008/053667. European Patent Office (acting as International Searching Authority), 15 pgs. 2008.

P.J. Holloway et al, Effects of some agricultural tank-mix adjuvants on the deposition efficiency of aqoueus sprays on foliage, Crop Protection, vol. 19, No. 1, 2000, pp. 27-37, XP002513889.

* cited by examiner

Average Velocity for the Spary Cloud (m/s) X-scan

Nozzle: Teejet KR8003VS
@ 40 psi at a height of 30 cm

Velocity of Spray Droplets(m/secs)

| | Water | PowerMAX | Lecithin adjuvant blend (1qt/100gal) & PowerMAX |

FIG. 2

ADJUVANTS AND METHODS OF USING THEM

CROSS-REFERENCE TO RELATED APPLICATIONS

This application claims the benefit of U.S. Provisional Application No. 60/889,422, filed Feb. 12, 2007, the contents of the entirety of which are incorporated by this reference.

TECHNICAL FIELD

This invention is directed towards a process for producing bio-based and biodegradable microemulsions comprising agricultural adjuvants, compositions and uses thereof. The invention also relates to methods of using such microemulsions to disperse a compound in water.

BACKGROUND

U.S. Pat. No. 6,348,434 describes non-aqueous emulsifiable concentrates for herbicidally active compounds which contain alkyl pheonxyalkanoates and benzene sulfonate. However, these compounds have environmental implications and use aromatic compounds such as benzene sulfonate. Similarly, patent application WO 98/48624 describes an ethoxylated nonyl phenol phosphate ester as an anionic surfactant. However, nonyl phenol is classified by the U.S. Environmental Protection Agency as an "inert of toxicological concern" that must be identified on pesticide labels. Nonyl phenol esters may damage the environment due to their capability to form toxic metabolites and their use is not favored due to their suspected estrogenic activity.

Thus, a need exists for a bio-based adjuvant system that does not contain nonyl phenol ethoxylates or other aromatic compounds that have environmental implications, yet provides the desired dispersability characteristics.

SUMMARY OF THE INVENTION

The present invention fulfills this need and discloses environmentally friendly adjuvants and/or surfactants.

In one embodiment, a composition comprises an acidifier, an emulsifier, a co-surfactant and water.

In another embodiment, a process comprises mixing an emulsifier with a co-surfactant, thus forming a blend, and mixing an acidifier and water with the blend, thus forming an adjuvant composition.

In an additional embodiment, a composition comprises propionic acid, an emulsifier, vegetable fatty acids, water and a compound selected from the group consisting of sorbitan monostearate, polyoxyethylene ester of rosin, polyoxyethylene dodecyl mono ether, polyoxyethylene-polyoxypropylene block copolymer, polyoxyethylene monolaurate, polyoxyethylene monohexadecyl ether, polyoxyethylene monooleate, polyoxyethylene mono(cis-9-octadecenyl) ether, polyoxyethylene monostearate, polyoxyethylene monooctadecyl ether, polyoxyethylene dioleate, polyoxyethylene distearate, polyoxyethylene sorbitan monolaurate, polyoxyethylene sorbitan monooleate, polyoxyethylene sorbitan monopalmitate, polyoxyethylene sorbitan monostearate, polyoxyethylene sorbitan trioleate, polyoxyethylene sorbitan tristearate, polyglycerol ester of oleic acid, polyoxyethylene sorbitol hexastearate, polyoxyethylene monotetradecyl ether, polyoxyethylene sorbitol hexaoleate, fatty acids, tall-oil, hexaester with sorbitol, ethoxylated castor oil, ethoxylated soybean oil, ethoxylated polyoxyethylene sorbitol tetraoleate, fatty acids, mixed esters with glycerol and polyethylene glycol, alcohols, C9-C16 ethoxylated derivatives of any thereof, and combinations of any thereof.

In yet a further embodiment, a composition consists essentially of an acidifier, an emulsifier, a co-surfactant and water.

Other embodiments of the present invention will be apparent to those skilled in the art form and from the descriptions, which follow herein.

DESCRIPTION OF THE DRAWINGS

FIGS. 1-5 represent results of various studies performed on one embodiment of an adjuvant composition of the present invention.

DETAILED DESCRIPTION

Figure 1:
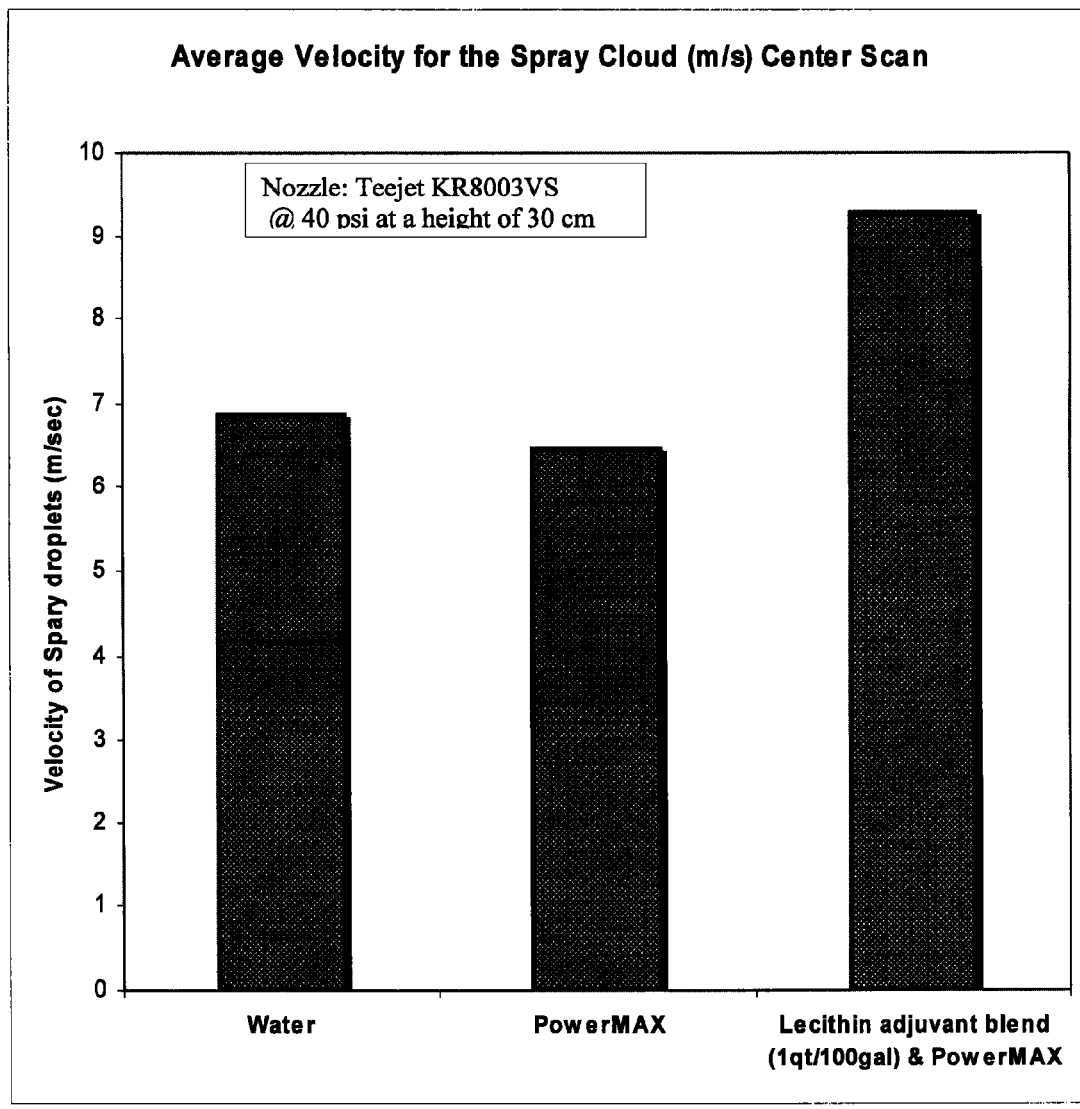
Figure 3:
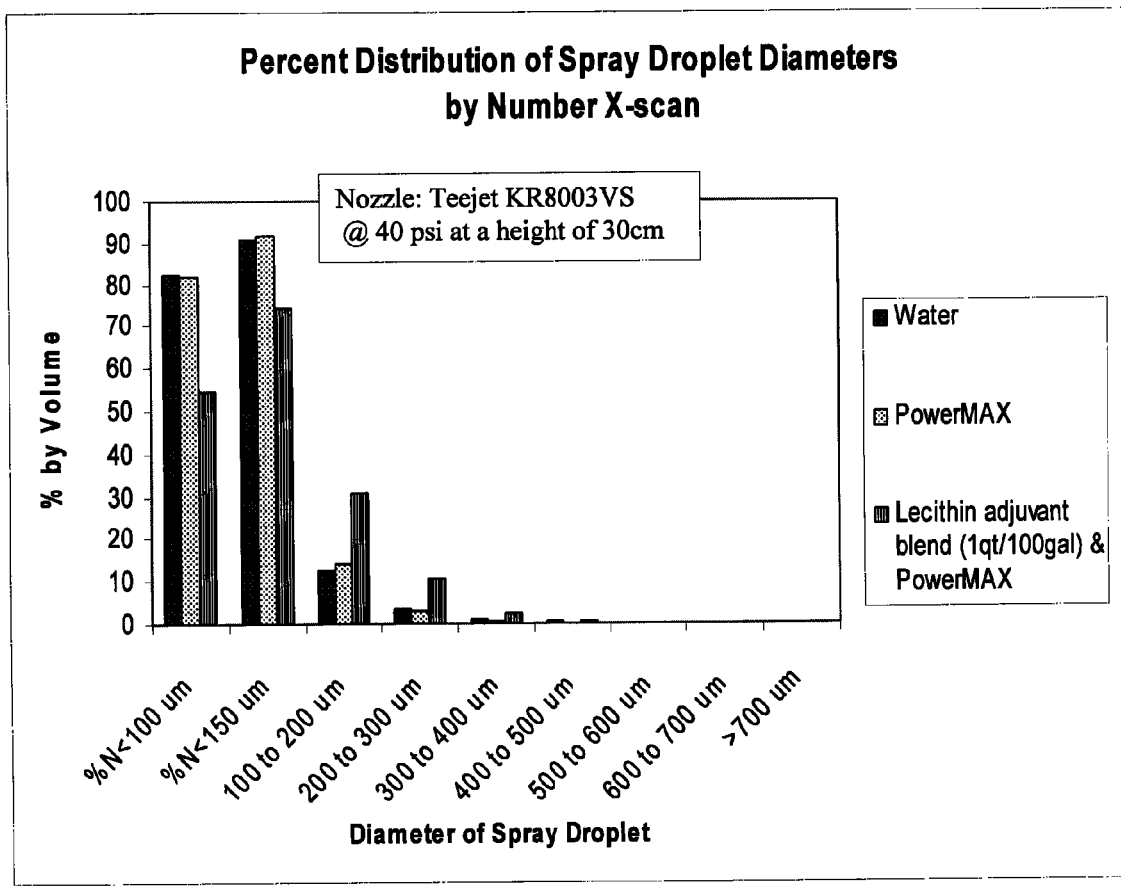
Figure 4:
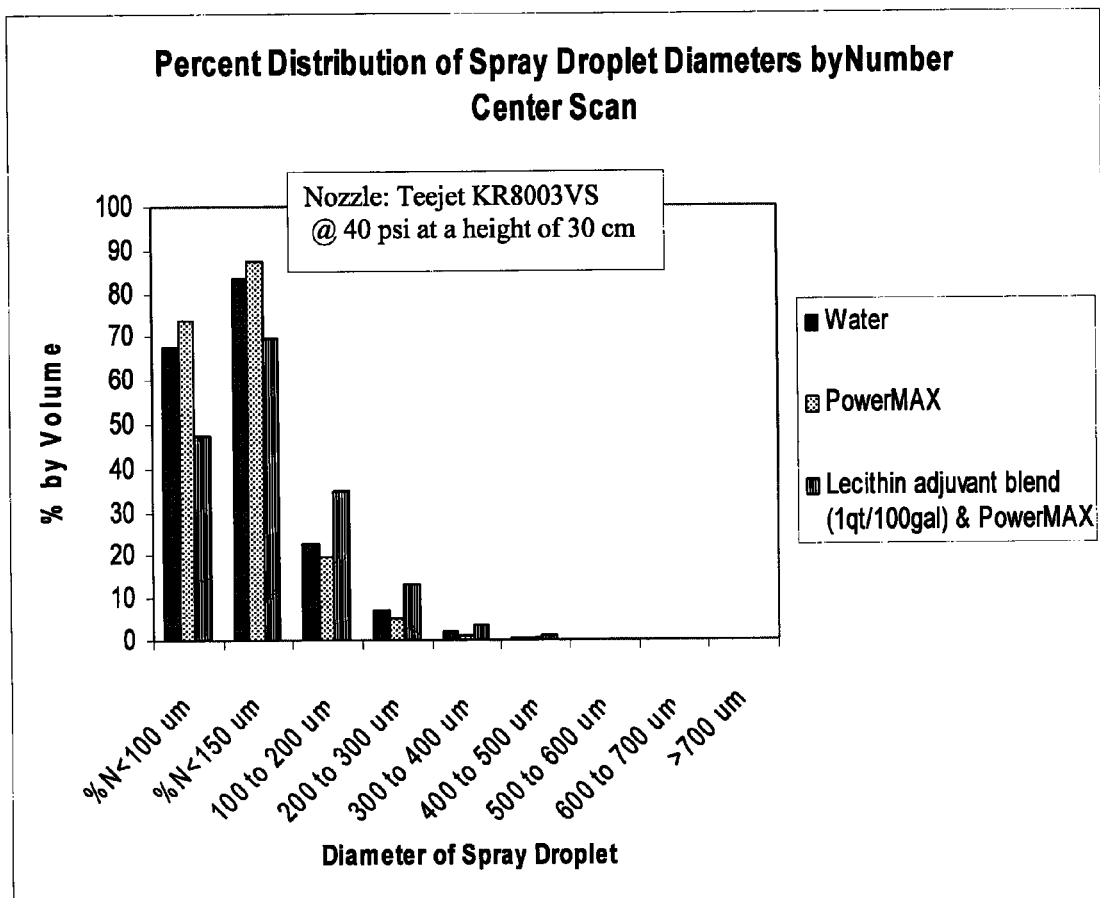
Figure 5:
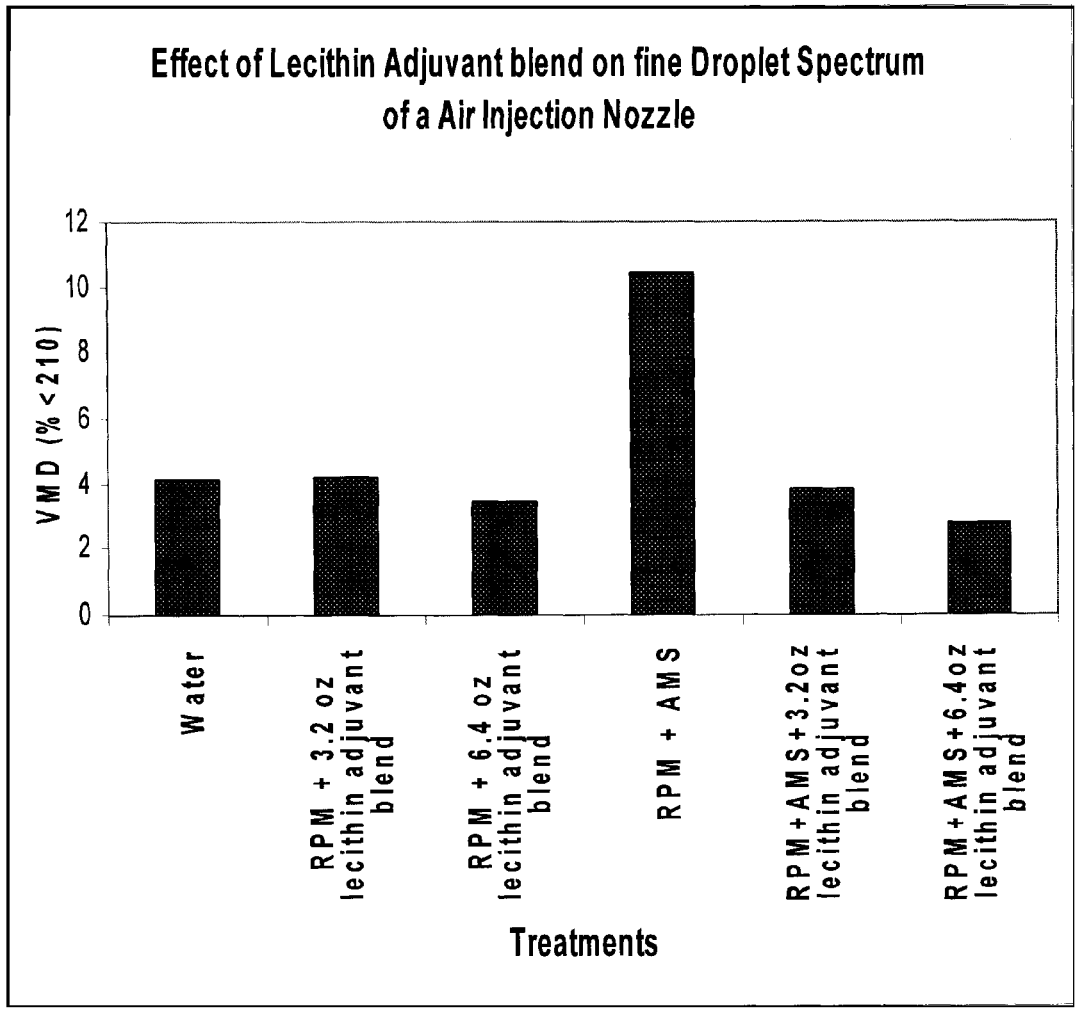

Adjuvants and surfactants are spray solution additives and are considered to be any product added to an agrochemical solution including, but not limited to, biocides, pesticides, herbicides, fungicides, and miticides to improve the performance of a spray solution containing the agrochemical solution. Examples of adjuvants include, but are not limited to, compatibility agents (used to aid mixing two or more herbicides in a common spray solution), drift retardants (used to decrease the potential for herbicide drift), suspension aids (used to aid mixing and suspending herbicide formulations in solution), spray buffers (used to change the spray solution acidity), and surfactants.

Because post emergence herbicide effectiveness is greatly influenced by plant factors such as age, size and the growing conditions of the plant encountered before application, herbicide performance can vary. One way to minimize the variations in post emergence herbicide performance is to use an adjuvant or surfactant in the spray solution. Adjuvants generally improve the effectiveness of post emergence herbicides.

An adjuvant is any additive used in conjunction with a pesticide to increase biological activity and/or to modify various physical properties of a spray solution containing the biocide, fungicide, nematicide, herbicide, pesticide, insecticide or combination of any thereof. Adjuvants and surfactants are added to spray solutions to improve the performance of crop protection compounds (herbicides). Adjuvants also play a key role in controlling the variables including, but not limited to, pesticide stability, solubility, compatibility, penetration, spreading, wetting, coverage, and drift. Surfactants act as an adjuvant that reduces surface tension between the spray solution droplets and the pest target's surface, thus, providing greater coverage.

Surfactants are added to oil adjuvants as emulsifiers to obtain an even distribution of the adjuvant in water. In one embodiment, the adjuvants can affect herbicide performance in many ways such as the spread of spray droplets on the leaf surface, the retention of spray droplets on the leaf, and penetration of the herbicide in the spray droplet through the plant cuticle. Surfactants form a "bridge" between chemicals that don't mix such as, for example, water and oil or water and the wax on a leaf surface. Surfactants lower the surface tension of spray droplets of the herbicide during application and allow for more complete spray coverage and sticking of the herbicide on the plant surface of the droplets. Some herbicides may also contain fatty acids to further improve herbicide retention and penetration. When there are many cations present in the water, as is the case with hard water, the cations including, without limitation, sodium, potassium, calcium, and magnesium can react with the herbicide, thus decreasing the uptake and effectiveness of the herbicide. For instance, a high level of calcium in water (hard water) reduces the control efficacy of glyphosates. Similarly, sodium bicarbonate reduces the efficacy of sethoxydim. A water conditioner, such as ammonium sulfate (which has utility as a nitrogen fertilizer) can negate this effect for glyphosate and sethoxydim. Also, herbicides are generally applied with fertilizers or fertilizer solutions, especially in agricultural settings. Compatibility agents are used to keep these herbicides in suspension. Most herbicides can be applied in nitrogen solutions without any compatibility problems, but compatibility may be poor when water contains high levels of various salts (hard water), or when the water is very cold.

In one embodiment, an adjuvant microemulsion that is based on bio-degradable and bio-renewable ingredients that can be easily mixed with a biological or chemical agent such as a biocide, fungicide, nematacide, herbicide, pesticide or insecticide that is to be dispersed in water prior to application is disclosed. In another embodiment, a method is described for mixing a composition comprising an acidifier, lecithin, water and a co-surfactant in water, dispersing the composition in water and applying the dispersed composition to soil.

Also, yet another embodiment of this invention describes a process for producing a microemulsion by mixing lecithin with a surfactant, thus forming a lecithin co-surfactant blend, and mixing an acidifier with the lecithin co-surfactant blend in presence of water, thus forming an adjuvant system. One aspect of this embodiment describes using vegetable fatty acids, soy fatty acids, derivatives of any thereof, and combinations of any thereof as additional components of the adjuvant system.

In another embodiment, a microemulsion comprising an acidifier, lecithin, water and a compound selected from the group consisting of triglycerides, diglycerides, sugar alcohols, ethoxylated monoglycerides, fatty acid ethoxylates, sorbitan monoester, polyoxyethylene alkyl ethers, polyoxyethylene alkyl esters, sorbitan alkyl esters, polyoxyethylene sorbitan alkyl esters, glycerol esters, short chain fatty alcohols, acids, esters, glycerols, glycols, derivatives of any thereof, and combinations of any thereof is disclosed.

In another embodiment, a microemulsion comprising an acidifier, lecithin, water and a compound selected from the group consisting of sorbitan monostearate, polyoxyethylene ester of rosin, polyoxyethylene dodecyl mono ether, polyoxyethylene-polyoxypropylene block copolymer, polyoxyethylene monolaurate, polyoxyethylene monohexadecyl ether, polyoxyethylene monooleate, polyoxyethylene mono(cis-9-octadecenyl)ether, polyoxyethylene monostearate, polyoxyethylene monooctadecyl ether, polyoxyethylene dioleate, polyoxyethylene distearate, polyoxyethylene sorbitan monolaurate polyoxyethylene sorbitan monooleate, polyoxyethylene sorbitan monopalmitate, polyoxyethylene sorbitan monostearate, polyoxyethylene sorbitan trioleate, polyoxyethylene sorbitan tristearate, polyglycerol ester of oleic acid, polyoxyethylene sorbitol hexastearate, polyoxyethylene monotetradecyl ether, polyoxyethylene sorbitol hexaoleate, fatty acids, hexaester with sorbitol, ethoxylated castor oil, ethoxylated soybean oil, ethoxylated polyoxyethylene sorbitol tetraoleate, fatty acids, tall-oil, mixed esters with glycerol and polyethylene glycol, alcohols, C9-16 and ethoxylated derivatives of any thereof, and combinations of any thereof is disclosed.

In yet other embodiments, adjuvant systems including micro emulsions that may be applied as fertilizer concentrates, in bioremediation applications, in biocide applications and as water conditioning agents are disclosed. One aspect of this embodiment describes the use of bio-based and bio-renewal components for preparing such adjuvant systems.

Microemulsions are clear, isotropic, thermodynamically stable liquid mixtures including oil, water and a surfactant. The water phase may contain salt(s) and/or other ingredients. Micro emulsions may be prepared from a large number of components. In contrast to ordinary emulsions, micro emulsions form upon simple mixing of the components and do not require high shear conditions. In ternary systems, such as micro emulsions, where two immiscible phases (water and 'oil') are present next to the surfactant phase, the surfactant molecules form a monolayer at the interface between oil and water, with the hydrophobic tails of the surfactant molecules dissolved in the oil phase and the hydrophilic head groups in the aqueous phase. Comparable to the binary systems (water/surfactant or oil/surfactant), self-assembled structures of different morphologies can be obtained ranging from (inverted) spherical and cylindrical micelles to lamellar phases and bicontinuous microemulsions. A water-in-oil microemulsion is an optically transparent mixture including oil, water, and surfactant. Water droplets are in a continuous oil phase stabilized by surfactant.

In one embodiment, an adjuvant system is a microemulsion and may be used as a surfactant to enhance the activity and effectiveness of agricultural chemicals, such as herbicides, defoliants, desiccants, plant growth regulators, insecticides, fungicides, foliar nutrients, acaracides, and combinations of any thereof. The adjuvant system provides more uniform coverage by decreasing surface tension of spray solutions, thus, aiding in penetration. The adjuvant system may also be used as an acidifying agent to lower pH of spraying solutions, thus, preventing alkaline hydrolysis of pesticides sensitive to high pH.

In one embodiment, a lecithin co-surfactant blend is produced. Such a blend is produced by blending lecithin with a surfactant having a HLB in the range of about 10.0 to 18.0, optionally, in the presence of a co-solvent including, but not limited to, short chain fatty alcohols, acids, ester, glycerols, glycols or any combinations thereof. The co-surfactant blend may include ethoxylated monoglycerides or fatty acid ethoxylate, soybean oil, propylene glycol or any combination thereof. Several surfactants may be used for the blend such as, for example, polyoxyethylene alkyl esters, sorbitan alkyl esters, polyoxyethylene sorbitan alkyl esters, glycerol esters, sugar esters, polyglycerol esters, derivatives of any thereof or combinations of any thereof. In another embodiment, surfactants which have HLB value of 12 to 16 may be used. The surfactant blend may be produced by mixing lecithin, such as for example fluidized lecithin, crude lecithin, de-oiled lecithin or any combination thereof, with a composition containing the surfactants and co-solvents. In one embodiment, the range of such blends may comprise lecithin in a concentration of between about 50 percent by weight to about 90 percent by weight with the remainder of the blend comprising a co-surfactant.

The lecithin co-surfactant blend may be intermixed with an acidifier in presence of water to produce an adjuvant system. In one embodiment, levels of such blends that may be used are between about 30 percent to about 45 percent by weight of the acidifier in water, wherein the acidifier in water is added to the lecithin co-surfactant blend.

The lecithin co-surfactant blend or the adjuvant system with the lecithin co-surfactant may be achieved by a variety of techniques including, but not limited to, blending, mixing, shear mixing, turbulizing, stirring, homogenizing or any combinations thereof. In one embodiment, mixing times that may be used for producing these blends may be at least 30 minutes. In another embodiment, a time period of about 30 minutes to about 3 hours at temperatures sufficient to produce uniform mixing may also be used. In one embodiment, temperatures between 25° C. to 60° C. may be used. Such conditions are a result of cause variable effect and may be optimized based on the type and concentrations of co-surfactants used to produce the blends.

The co-surfactant used may also contain propylene glycol, ethylene glycol, glycerol, short chain fatty acids, esters or any combinations thereof. The glycols or glycerol used herein may be of a bio-based origin. Various embodiments of the present disclosure also relate to a biobased glycerol, a biobased propylene glycol and a biobased ethylene glycol that are traditionally derived from petrochemical sources. In particular, biobased propylene glycol and biobased ethylene glycol can be produced by hydrogenolysis of polyols derived from biological sources (i.e., bioderived). The product mixture from the hydrogenolysis of bioderived polyols and the products produced therefrom may be differentiated from petroleum derived products, for example, by their carbon isotope ratios using ASTM International Radioisotope Standard Method D 6866. As used herein, the term "bioderived" means derived from or synthesized by a renewable biological feedstock, such as, for example, an agricultural, forestry, plant, bacterial, or animal feedstock.

In one embodiment, the adjuvant system may be a microemulsion comprising a first ingredient and at least one other secondary ingredient. In one embodiment, the first ingredient may be an acidifier. In various embodiment, the secondary ingredients may be at least one of the following compounds: an emulsifier, a co-surfactant, a vegetable fatty acid, a soy fatty acid, alcohols, acids, esters, glycerols, glycols, water, derivatives of any thereof, or combinations of any thereof. In another embodiment, the adjuvant system is intermixed with a biological agent, a chemical agent or a fertilizer to enhance its application properties to plant or soil material.

In one embodiment, the first ingredient may be an acidifier such as, for example, propionic acid or any other effective acidifier agent. Certain aspects of this embodiment may use any other suitable acid including, but not limited to, methyl acetic acid, acetic acid, lactic acid, fumaric acid, citric acid, phosphoric acid, ascorbic acid or any combination there of as the acidifier agent.

Other embodiments use secondary ingredients such as vegetable fatty acids (e.g., soy fatty acids), derivatives of any thereof and combinations of any thereof. Any suitable plant based fatty acids including, without limitation, butyric acid, caproic acid, caprylic acid, capric acid, lauric acid, myristic acid, palmitic acid, stearic acid, arachic acid, behenic acid, lignoceric acid, hexacosanoic acid, octacosanoic acid, triacontanoic acid and n-dotriacontanoic acid, and those having an odd number of carbon atoms, such as propionic acid, n-valeric acid, enanthic acid, pelargonic acid, hendecanoic acid, tridecanoic acid, pentadecanoic acid, heptadecanoic acid, nonadecanoic acid, heneicosanoic acid, tricosanoic acid, pentacosanoic acid, heptacosanoic acid, isobutyric acid, isocaproic acid, isocaprylic acid, isocapric acid, isolauric acid, 11-methyldodecanoic acid, isomyristic acid, 13-methyl-tetradecanoic acid, isopalmitic acid, 15-methyl-hexadecanoic acid, isostearic acid, 17-methyloctadecanoic acid, isoarachic acid, 19-methyl-eicosanoic acid, a-ethyl-hexanoic acid, a-hexyldecanoic acid, a-heptylundecanoic acid, 2-decyltetradecanoic acid, 2-undecyltetradecanoic acid, 2-decylpentadecanoic acid, 2-undecylpentadecanoic acid, Fine oxocol 1800 acid (product of Nissan Chemical Industries, Ltd.), 6-methyl-octanoic acid, 8-methyl-decanoic acid, 10-methyl-dodecanoic acid, 12-methyl-tetradecanoic acid, 14-methyl-hexadecanoic acid, 16-methyl-octadecanoic acid, 18-methyl-eicosanoic acid, 20-methyl-docosanoic acid, 22-methyl-tetracosanoic acid, 24-methyl-hexacosanoic, 26-methyloctacosanoic acid including 4-decenoic acid, caproleic acid, 4-dodecenoic acid, 5-dodecenoic acid, lauroleic acid, 4-tetradecenoic acid, 5-tetradecenoic acid, 9-tetradecenoic acid, palmitoleic acid, 6-octadecenoic acid, oleic acid, 9-octadecenoic acid, 11-octadecenoic acid, 9-eicosenoic acid, cis-11-eicosenoic acid, cetoleic acid, 13-docosenoic acid, 15-tetracosenoic acid, 17-hexacosenoic acid, 6,9,12,15-hexadecatetraenoic acid, linoleic acid, linolenic acid (18:3 n3), gamma linolenic acid (18:3 n6), α-eleostearic acid, gadoleic acid (20:1), α-eleostearic acid, punicic acid, 6,9,12,15-octadecatetraenoic acid, parinaric acid, 5,8,11,14-eicosatetraenoic acid, erucic acid, 5,8,11,14,17-eicosapentaenoic acid (EPA), 7,10,13,16,19-docosapentaenoic acid, 4,7,10,13,16,19-docosahexaenoic acid (DHA), α-hydroxylauric acid, α-hydroxymyristic acid, α-hydroxypalmitic acid, α-hydroxystearic acid, ω-hydroxylauric acid, α-hydroxyarachic acid, 9-hydroxy-12-octadecenoic acid, ricinoleic acid, α-hydroxybehenic acid, 9-hydroxy-trans-10,12-octadecadienic acid, kamolenic acid, ipurolic acid, 9,10-dihydroxystearic acid, 12-hydroxystearic acid, oxalic acid, citric acid, phosphoric acid, malonic acid, succinic acid, glutaric acid, adipic acid, pimelic acid, suberic acid, azelaic acid, sebacic acid, D,L-malic acid, or combinations of any thereof and the like may be used.

In other embodiments, the secondary ingredients may be dissolved in water. Generally, the microemulsion adjuvant compositions are provided separately and a penetrant (such as a co-surfactant) is combined when used. The final compositions may be diluted in water and sprayed or poured onto the soil. In one embodiment, ingredients may be present in one phase for ease of use and are ready to deliver to the soil by diluting with water. In one embodiment, concentrations of the first ingredient in the aqueous solution may range from 0.1 to 20 percent. It will be apparent by those of ordinary skill in the art that the percentages and methods used for application will vary with the type of crop, type of control desired, and/or other conditions and may be optimized using routine experimentation. The co-surfactants used may also include without limitation, for example, polyoxyethylene derivatives of sorbitan monoester, such as a polyethylene oxide of sorbitan fatty acid esters (e.g., sorbitan monopalmitate, sorbitan monooleate, sorbitan monostearate). These compounds are available under the trade name of "TWEEN" of Uniqema Company (a Delaware Corporation) such as TWEEN 60 or TWEEN 80. Any other suitable surfactant in the desired HLB range may be used. Such surfactants are available from numerous suppliers such as, for example, BASF (Florham Park, N.J.), Lonza (Allendale, N.J.), Stepan (Northfield, Ill.), Kerry (Beloit, Wis.).

In another embodiment, mixed surfactants (surfactant mixtures) in the given HLB range of 10-18 may be used to enhance the solubilization properties of the adjuvant system, which could be used to improve the efficacy and penetration of the herbicide.

Another embodiment of the invention enables the use of hard (e.g., well) water for applying a herbicide to soil. Dispersibility of the composition of the present invention in hard water is important because of the cost associated with treating water to reduce its hardness. Well water high in mineral (e.g., calcium, magnesium and iron) content may also be used. The adjuvant system described herein, upon mixing with the herbicide may be used at rates such as from about 6 pounds per acre to about 300 pounds per acre upon dilution in water. In certain embodiments, the adjuvant system may be used at rates of one pound per acre or less depending upon the amount necessary to attain effective control by any application technique in which the adjuvant system and biocides are brought in mutual contact, such as to the foliage of the plant or grass, to the soil itself, or other plant pest desired to be controlled.

In another embodiment, the compositions of the present invention may be used in conjunction with various organic fertilizers such as those described in U.S. patent application Ser. No. 11/549,470 filed Oct. 13, 2006, entitled "Fertilizer Compositions and Methods of Using," the contents of the entirety of which is incorporated by this reference.

The teachings of this invention may also be used in conjunction with any biological or chemical agent including, but not limited to, a biocide, fungicide, nematacide, herbicide, pesticide, insecticide or combination of any thereof that may be dispersed in water prior to application. For instance, substances used in crop protection which may be dispersed in water prior to application may be developed by the teachings of this invention. A blend of lecithin and a co-surfactant may be prepared and blended with the biological or chemical agent that is required for application to produce a stable dispersion in water. In one embodiment, the dispersion may also be dispersed in hard water.

In one embodiment, a composition consists essentially of an acidifier, an emulsifier, a co-surfactant and water.

In another embodiment, a process for producing a product includes mixing an emulsifier with a co-surfactant, thus forming a blend. The blend is mixed with an acidifier and water, thus forming an adjuvant composition.

In a further embodiment, a composition comprises propionic acid, an emulsifier, water and a compound selected from the group consisting of triglycerides, diglycerides, sugar alcohols, ethoxylated monoglycerides, fatty acid ethoxylates, sorbitan monoester, polyoxyethylene alkyl ethers, polyoxyethylene alkyl esters, sorbitan alkyl esters, polyoxyethylene sorbitan alkyl esters, glycerol esters, short chain fatty alcohols, acids, esters, glycerols, glycols, derivatives of any thereof, and combinations of any thereof.

In one embodiment, a composition includes propionic acid, an emulsifier, a vegetable fatty acid, water and a compound selected from the group consisting of sorbitan monostearate, polyoxyethylene ester of rosin, polyoxyethylene dodecyl mono ether, polyoxyethylene-polyoxypropylene block copolymer, polyoxyethylene monolaurate, polyoxyethylene monohexadecyl ether, polyoxyethylene monooleate, polyoxyethylene mono(cis-9-octadecenyl) ether, polyoxyethylene monostearate, polyoxyethylene monooctadecyl ether, polyoxyethylene dioleate, polyoxyethylene distearate, polyoxyethylene sorbitan monolaurate polyoxyethylene sorbitan monooleate, polyoxyethylene sorbitan monopalmitate, polyoxyethylene sorbitan monostearate, polyoxyethylene sorbitan trioleate, polyoxyethylene sorbitan tristearate, polyglycerol ester of oleic acid, polyoxyethylene sorbitol hexastearate, polyoxyethylene monotetradecyl ether, polyoxyethylene sorbitol hexaoleate, fatty acids, tall-oil, hexaester with sorbitol, ethoxylated castor oil, ethoxylated soybean oil, ethoxylated polyoxyethylene sorbitol tetraoleate, fatty acids, mixed esters with glycerol and polyethylene glycol, alcohols, C9-C16 ethoxylated derivatives of any thereof, and combinations of any thereof.

In yet a further embodiment, a composition includes propionic acid, an emulsifier, a vegetable fatty acid, water and a compound selected from the group consisting of sorbitan monostearate, polyoxyethylene ester of rosin, polyoxyethylene dodecyl mono ether, polyoxyethylene-polyoxypropylene block copolymer, polyoxyethylene monolaurate, polyoxyethylene monohexadecyl ether, polyoxyethylene monooleate, polyoxyethylene mono(cis-9-octadecenyl) ether, polyoxyethylene monostearate, polyoxyethylene monooctadecyl ether, polyoxyethylene dioleate, polyoxyethylene distearate, polyoxyethylene sorbitan monolaurate polyoxyethylene sorbitan monooleate, polyoxyethylene sorbitan monopalmitate, polyoxyethylene sorbitan monostearate, polyoxyethylene sorbitan trioleate, polyoxyethylene sorbitan tristearate, polyglycerol ester of oleic acid, polyoxyethylene sorbitol hexastearate, polyoxyethylene monotetradecyl ether, polyoxyethylene sorbitol hexaoleate, fatty acids, tall-oil, hexaester with sorbitol, ethoxylated castor oil, ethoxylated soybean oil, ethoxylated polyoxyethylene sorbitol tetraoleate, fatty acids, mixed esters with glycerol and polyethylene glycol, alcohols, C9-C16 ethoxylated derivatives of any thereof, and combinations of any thereof.

In an additional embodiment, a composition consists essentially of propionic acid, an emulsifier, water and a compound selected from the group consisting of ethoxylated monoglycerides, fatty acid ethoxylates, sorbitan monoester, polyoxyethylene alkyl ethers, polyoxyethylene alkyl esters, sorbitan alkyl esters, polyoxyethylene sorbitan alkyl esters, propylene glycol, glycerol, glycols derivatives of any thereof, and combinations of any thereof.

In one embodiment, a composition includes an emulsifier, and an ethoxylated monoglyceride, a fatty acid ethoxylate or a combination thereof. The composition further includes propionic acid and water.

In various embodiments, the emulsifier comprises lecithin. Other embodiments include the use of the compositions of the present invention for dispersing a compound in water.

EXAMPLES

The following non-limiting examples are provided to further describe the invention. Those of ordinary skill in the art will appreciate that several variations these Examples are possible within the spirit of the invention.

Example 1

This example describes one embodiment of a method of making AN adjuvant formulation. An adjuvant blend was prepared by mixing YELKIN T brand lecithin (a crude lecithin available from Archer Daniels Midland Company, Decatur, Ill.) in an amount of 35% by weight; propionic acid (available from Fisher Scientific, Fairlawn, N.J.) in an amount of 35% by weight; vegetable fatty acids in an amount of 3.5% (available from Chemtura, Middlebury, Conn.) by weight of lecithin with fatty acid ethoxylate (Ninex MT-610 available from Stepan, Northfield, Ill.,) 10% by weight.

The ingredients were mixed and heated to 50° C. under constant stirring for between 30 minutes to 60 minutes. 20% water by weight was slowly added to the mixture with constant stirring for about one half hour. The fatty acid ethoxylate used in this example is an agricultural emulsifier and is approved by the EPA as inert ingredient under U.S. EPA §40 CFR 180.910, U.S. EPA §21 CFR 176.210, 175.105. A stable microemulsion was obtained that may be used as an agricultural adjuvant.

Example 2

This example describes one embodiment of a method of making an adjuvant concentrate formulation. An adjuvant concentrate blend was prepared by mixing YELKIN SS brand lecithin (a bleached, fluidized lecithin available from Archer Daniels Midland Company, Decatur, Ill.) in an amount of 35% by weight; and fatty acid ethoxylate (Ninex MT-610 available from Stepan, Northfield, Ill.) 10% by weight.

The ingredients were mixed and heated to 50° C. under constant stirring for between 30 minutes to 60 minutes. 35% propionic acid by weight of the mixture (available from Fisher Scientific, Fairlawn, N.J.) were slowly added followed by 20% water by weight on constant stirring at 50° C. for about one half hour. The fatty acid ethoxylate used in this example is a non-APE agricultural emulsifier and is approved by the EPA as inert ingredient under U.S. EPA §40 CFR 180.910, U.S. EPA §21 CFR 176.210, 175.105. A stable microemulsion was obtained that may be used as an agricultural adjuvant.

Example 3

This example describes one embodiment of a method of making an adjuvant concentrate formulation. An adjuvant concentrate blend was prepared by mixing YELKIN TS brand lecithin (fluidized lecithin available from Archer Daniels Midland Company, Decatur, Ill.) in an amount of 35% by weight; and fatty acid ethoxylate (Ninex MT-610 available from Stepan, Northfield, Ill.) 10% by weight.

The ingredients were mixed and heated to 50° C. under constant stirring for between 30 minutes to 60 minutes. 35% propionic acid (available from Fisher Scientific, Fairlawn, N.J.) by weight of the mixture were added slowly followed by 20% water by weight on constant stirring at 50° C. for about one half hour. The fatty acid ethoxylate used in this example is a non-APE agricultural emulsifier and is approved by the EPA as inert ingredient under U.S. EPA §40 CFR 180.910, U.S. EPA §21 CFR 176.210, 175.105. A stable microemulsion was obtained that may be used as an agricultural adjuvant.

Example 4

The composition produced by any of examples 1, 2 or 3 is diluted with an herbicide in water, optionally hard water, to form an emulsion comprising between 0.1 percent to 1.0 percent by weight of the microemulsion in water. The microemulsion may be applied in the amount of 0.1 gallons to 2.0 gallons per acre of land area depending upon the biocide control required.

Example 5

The surface tension of the composition of Example 1 in different dilution concentrations was determined. The dilution concentrations are listed in Table 1. The surface tension was measured using a CSC-DuNouy Tensiometer (ASTM D1331). The contact angle of a drop of each dilution on parafilm was measured with a Ramé-Hart Contact Angle Goniometer. The angle of each drop relative to the surface of the parafilm was measured at 30, 60 and 90 seconds after formation of the drop.

TABLE 1

| Dilution Concentration % | Surface Tension dynes/cm | Contact Angle on parafilm, degrees | |
|---|---|---|---|
| | | 60 secs | 90 sec |
| 0.01 | 45.9 | 87 | 87 |
| 0.10 | 41.5 | 58 | 55 |
| 0.25 | 38.8 | 58 | 52 |

The contact angle (CA) is a profile measurement of a drop of liquid in contact with a solid surface. When a surfactant or wetting agent is introduced into the liquid, the surface tension is reduced and the liquid droplet becomes flatter. The lower the contact angle produced by the surfactant, the greater the spreading and coverage properties of the liquid including such surfactant. Water has a contact angle of about 93 degrees, and a typical surfactant influences the contact angle from about 30-45 degrees. The contact angle of a crop oil concentrate or methylated seed oil is about 58 and the adjuvant composition of this example has similar surface wetting properties. Further, the surface tension data of the adjuvant composition of this example is typical of a conventional wetting agent (i.e., 30-50 dynes/cm).

Example 6

The ability of the composition of Example 1 to function as an adjuvant with ROUNDUP POWERMAX brand herbicide, available from the Monsanto Company was determined. In this example, the compositions studied were water, ROUNDUP POWERMAX brand herbicide and a mixture of ROUNDUP POWERMAX brand herbicide with the composition of Example 1.

The nozzle used in this example was a Teejet XR8003VS. The compositions were up made up with tap water at 20° C. Each composition was sprayed through the nozzle tip at 40 psi (pounds per square inch) at a height of 30 cm (centimeters) above the probe volume of the Aerometrics PDPA laser system. The size range of droplets scanned were between 25.7 µm (micrometers)-900.0 µm. The voltage for the photo-multiplier tube (PMT) was set to 325 V (volts). Two types of measurements were made for each treatment under the x-y axis intersection point, and a scan down the length of the long x-axis to yield an overall global sample.

Results of the studies of this example are presented in FIGS. 1-5. The average velocity for the entire spray cloud (m/s) measured using a PDPA-100D system are shown in FIGS. 1 and 2. The data clearly shows the effect that the adjuvant composition of this example has on atomization wherein the adjuvant composition performs in a manner similar to conventional wetting agents. The effect of compositions of this example is clearly seen in the number median diameter (NMD), velocity and drift potential as estimated by percent volume <150 µm. In this example, the adjuvant composition clearly elevated the NMD as compared to water and POWERMAX brand herbicide, raised the spray cloud velocity and reduced the spray volume contained in droplets that are <150 µm. The adjuvant composition further reduced the relative span as illustrated in FIGS. 3 and 4.

The data indicates that the percentage of droplets by volume of the ROUNDUP POWERMAX brand herbicide by itself as compared to the herbicide with the adjuvant composition of the present invention was as follows: for droplets less than <150 μm, the adjuvant composition reduced such droplets by a factor of two; and for droplets less than <100 μm, the adjuvant composition reduced such droplets by a factor of 3. As illustrated in FIG. 5, the droplet spectrum of the air injection nozzle is greatly improved in the presence of the adjuvant composition of this example. The data indicates that use of the adjuvant composition will result in better coverage of the agrochemical of the leaf, better penetration of the agrochemical in a canopy, as well as better efficacy, adhesion and retention of the agrochemical to the surface of the leaf.

Example 7

In this example, the effectiveness of the composition of Example 1 as an adjuvant with glyphosate on soybeans was evaluated. This example used randomized block testing and was performed in three replications with plot sizes of 10 by 25 feet.

The adjuvant composition of this example is a multifunctional lecithin based product that improves the performance of agricultural chemicals. The adjuvant composition is a strong acidifier and a good wetter/spreader at rates of at least one pint per 100 gallons of water. The adjuvant composition of this example has water conditioning properties and also serves as a drift control agent when applied at a rate of one quart per gallon, as well as enabling improved coverage and deposition of the agricultural chemical with which the adjuvant composition is used. Another property of the adjuvant composition of this example is that the lecithin contained therein enables the agricultural chemical to penetrate the leaf cuticle and maximizes the penetration of the agricultural chemical through the waxy layer of the foliage while maintaining the integrity of the plant's protective wax layer. This improves the performance of the agricultural chemical which function by penetrating into the plant while greatly reducing burn potential to the plant.

The results of this example presented in Table 2 indicated that the adjuvant composition applied with glyphosate provided very good weed control and indicated weed kill for foxtail, velvet leaf, common waterhemp and common ragweed to be 99%, 99%, 97% and 99%, respectively after 21 days. This example also indicated that the adjuvant composition was very safe for soybeans since the percent phytotoxicity was determined to be 5% and 1.7% after 7 and 14 days, respectively, after application, and the percent phytotoxicity was further measured to be 0% at 21 and 28 days after application.

TABLE 2

Efficacy of Post Emergence applied Glyphosate with Lecithin adjuvant blend in Soybeans

| | | | % Mean Weed Control | | | | % Phytotoxicity |
|---|---|---|---|---|---|---|---|
| Application | Rates | Days after Applicatiotn | Foxtail | Velvetleaf | Common Waterhemp | Common Ragweed | Crop Soybean |
| K Glyphosate Salt | 0.75 lbs/acre | 7 | 86.7 | 55.0 | 83.3 | 82.5 | 5.0 |
| Lecithin adjuvant blend | 1 qt/100 gal | 14 | 99.0 | 97.0 | 97.7 | 99.0 | 1.7 |
| | | 21 | 99.0 | 97.0 | 97.7 | 99.0 | 0.0 |
| | | 28 | 99.0 | 91.7 | 96.3 | 99.0 | 0.0 |
| Razor | 0.75 lbs/acre | 7 | 85.0 | 81.7 | 71.7 | 80.0 | 5.0 |
| Exstra 4726 | 1 qt/100 gal | 14 | 99.0 | 93.3 | 94.7 | 97.7 | 10.0 |
| | | 21 | 99.0 | 91.7 | 91.7 | 99.0 | 18.3 |
| | | 28 | 99.0 | 93.0 | 95.0 | 98.0 | 23.0 |

| | | Weed Species | Height at Application |
|---|---|---|---|
| Crop: | Soybean | Faber's Foxtail | 25-30 in |
| Growth Stage: | R2 | Velvetleaf | 26-30 in |
| Height | 19-22 in | Common Waterhemp | 24-54 in |
| Application Method | Foliar Spray | Common Ragweed | 26-34 in |

As Table 2 indicates, the adjuvant composition of this example has a reduced phytotoxicity effect as compared to the commercially available adjuvant Razor exstra 4726.

The present invention has been described with reference to certain exemplary embodiments, compositions and uses thereof. However, it will be recognized by those of ordinary skill in the art that various substitutions, modifications or combinations of any of the exemplary embodiments may be made without departing from the spirit and scope of the invention. Thus, the invention is not limited by the description of the exemplary embodiment, but rather by the appended claims as originally filed.

What is claimed is:

1. An agrochemical composition comprising: a microemulsion that is a clear, isotropic, thermodynamically stable liquid, the microemulsion comprising: 35% crude lecithin; 3.5% fatty acids; an ester; 30-45% lactic acid; oil; and 10% ethoxylated monoglycerides; and an agrochemical solution selected from the group consisting of a biocide, herbicide, fungicide, nematicide, pesticide, and miticide; and water; wherein the microemulsion and the agrochemical solution are dispersed in the water.

2. The agrochemical composition of claim 1, wherein the microemulsion is present in the agrochemical composition at an amount of between 0.1-1.0% by weight.

3. The agrochemical composition of claim 1, wherein the fatty acids are selected from the group consisting of caproic acid, caprylic acid, capric acid, lauric acid, behenic acid, lignoceric acid, hexacosanoic acid, octacosanoic acid, triacontanoic acid and n-dotriacontanoic acid, and those having an odd number of carbon atoms including propionic acid, n-valeric acid, enanthic acid, pelargonic acid, hendecanoic acid, tridecanoic acid, pentadecanoic acid, heptadecanoic acid, nonadecanoic acid, heneicosanoic acid, tricosanoic acid, pentacosanoic acid, heptacosanoic acid, isobutyric acid, isocaproic acid, isocaprylic acid, isocapric acid, isolauric acid, 11-methyldodecanoic acid, isomyristic acid, 13-methyl-tetradecanoic acid, isopalmitic acid, 15-methyl-hexadecanoic acid, isostearic acid, 17-methyloctadecanoic acid, isoarachic acid, 19-methyl-eicosanoic acid, a-ethyl-hexanoic acid, a-hexyldecanoic acid, a-heptylundecanoic acid, 2-decyltetradecanoic acid, 2-undecyltetradecanoic acid, 2-decylpentadecanoic acid, 2-undecylpentadecanoic acid, isooctadecanoic acid, 6-methyl-octanoic acid, 10-methyl-dodecanoic acid, 12-methyl-tetradecanoic acid, 14-methyl-hexadecanoic acid, 16-methyl-octadecanoic acid, 18-methyl-eicosanoic acid, 20-methyl-docosanoic acid, 22-methyl-tetracosanoic acid, 24-methyl-hexacosanoic, 26-methyloctacosanoic acid, caproleic acid, lauroleic acid, 6-octadecenoic acid, 9-octadecenoic acid, 11-octadecenoic acid, 9-eicosenoic acid, cis-11-eicosenoic acid, cetoleic acid, 13-docosenoic acid, 15-tetracosenoic acid, 17-hexacosenoic acid, 6,9,12,15-hexadecatetraenoic acid, gamma linolenic acid (18:3 n6), α-eleostearic acid, gadoleic acid (20:1), α-eleostearic acid, punicic acid, 6,9,12,15-octadecatetraenoic acid, parinaric acid, 5,8,11,14-eicosatetraenoic acid, 7,10,13,16,19-docosapentaenoic acid, α-hydroxylauric acid, α-hydroxymyristic acid, α-hydroxypalmitic acid, α-hydroxystearic acid, ω-hydroxylauric acid, α-hydroxyarachic acid, 9-hydroxy-12-octadecenoic acid, ricinoleic acid, α-hydroxybehenic acid, 9-hydroxy-trans-10,12-octadecadienic acid, kamolenic acid, ipurolic acid, 9,10-dihydroxystearic acid, 12-hydroxystearic acid, oxalic acid, citric acid, phosphoric acid, malonic acid, succinic acid, glutaric acid, adipic acid, pimelic acid, suberic acid, azelaic acid, sebacic acid, D,L-malic acid, derivatives of any thereof, and combinations of any thereof.

4. The agrochemical composition of claim 1 further comprising polyoxyethylene sorbitan alkyl esters.

5. The agrochemical composition of claim 1 further comprising fatty acid ethoxylates.

* * * * *